United States Patent [19]

Potier et al.

[11] Patent Number: 4,737,586

[45] Date of Patent: Apr. 12, 1988

[54] PROCESS FOR THE PREPARATION OF BIS-INDOLIC COMPOUNDS

[75] Inventors: Pierre Potier; Nicole Langlois; Yves Langlois; Francoise Gueritte, all of Gif S/Yvette, France

[73] Assignee: Agence Nationale de Valorisation de la Recherche, Neuilly Sur Seine, France

[21] Appl. No.: 857,075

[22] Filed: Apr. 29, 1986

Related U.S. Application Data

[60] Division of Ser. No. 275,050, Jun. 18, 1981, which is a continuation of Ser. No. 105,572, Dec. 20, 1979, abandoned, which is a continuation of Ser. No. 645,071, Dec. 29, 1975, abandoned.

[30] Foreign Application Priority Data

Dec. 30, 1974 [FR] France ................ 74 43221

[51] Int. Cl.$^4$ ........................................... C07D 519/04
[52] U.S. Cl. ................................................. 540/478
[58] Field of Search ......................................... 540/478

[56] References Cited

U.S. PATENT DOCUMENTS

| | | |
|---|---|---|
| 4,029,663 | 6/1977 | Gutowski et al. ............... 540/478 |
| 4,143,041 | 3/1979 | Thompson ....................... 540/478 |
| 4,144,237 | 3/1979 | Kutney ............................ 540/478 |
| 4,199,505 | 4/1980 | Szantay et al. .................. 540/478 |
| 4,279,817 | 7/1981 | Kutney ............................ 540/478 |

FOREIGN PATENT DOCUMENTS 2558124  7/1976  Fed. Rep. of Germany ...... 540/478

OTHER PUBLICATIONS

Massin, et al., Bulletin des Societies d'Opthalmologie, 1972, 9–10, LXXII, pp. 889–892.

Chakraborty, et al., Indian J. Med. Res., 60, May 5, 1972, pp. 800–807.

Scott, et al., J. Am. Chem. Soc., vol. 100, No. 19, pp. 6253–6255, (09/13/78).

Potier et al, "Partial Synthesis of Vinblastine-Type Alkaloids", J.C.S. Chem. Comm., pp. 670–671 (1975).

Langlois et al, J. Am. Chem. Soc., vol. 98, No. 22, pp. 7017–7024 (1976).

Kutney et al, "Total Synthesis of Indole and Dihydroindole Alkaloids", Helvetica Chimica Acta, vol. 59, No. 8, pp. 2858–2882.

Kutney et al, "Studies on the Synthesis of Bisindole Alkaloids", II., Heterocycles, vol. 3, No. 8, pp. 639–649 (1975).

Neuss et al, Tetrahedron Letters, No. 7, pp. 783–787 (1968).

Treasurywala, "Studies Related to the Synthesis of Bisindole Alkaloids of the Indole–Indoline Type", Doctoral Thesis, University of British Columbia, Dec., pp. 143–152 and 188–190 (1973).

Rahman, Pakistan J. Sci. Ind. Res., vol. 14, No. 6, pp. 487–488, Dec., 1971.

Collection Czechoslov. Chem. Commun., vol. 39 (1974).

Kutney et al, Chemical Abstract 83:28420z (1975).
Potier et al, Chemical Abstract 86:29977k (1976).
Kutney et al, Chemical Abstract 84:59829q (1975).
Kutney et al, Chemical Abstract 85:160409y (1976).

Primary Examiner—Donald G. Daus
Assistant Examiner—Diana G. Rivers
Attorney, Agent, or Firm—Renner, Otto, Boisselle & Lyon

[57] ABSTRACT

The present invention relates to a process for the preparation of bis-indolic compounds, and the bis-indolic compounds produced by the process.

10 Claims, No Drawings

PROCESS FOR THE PREPARATION OF BIS-INDOLIC COMPOUNDS

This is a divisional of application Ser. No. 275,050, filed June 18, 1981, which is a continuation of application Ser. No. 105,572, filed Dec. 20, 1979, now abandoned, which is a continuation of application Ser. No. 645,071, filed Dec. 29, 1975, now abandoned. The disclosures of each of these prior applications are incorporated herein by reference.

The present invention relates to a process for the preparation of bis-indolic compounds and the bis-indolic compounds obtained by this process.

There exist natural alkaloids, such as vinblastine or vincristine which correspond to the formula

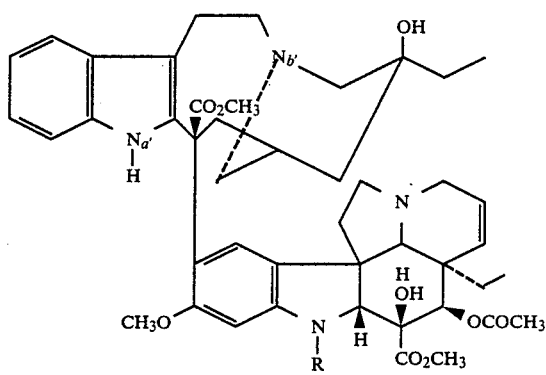

and which can be isolated from a number of species of Catharanthus, in particular C. roseus and which have anti-tumoral properties. However, these alkaloids are only present in very small quantities in the plant, thus it is of particular interest to be able to prepare semi-synthetic derivatives which have anti-tumoral properties and which can be easily obtained from more accessible products.

The process according to the present invention permits the preparation of compounds of the general formula

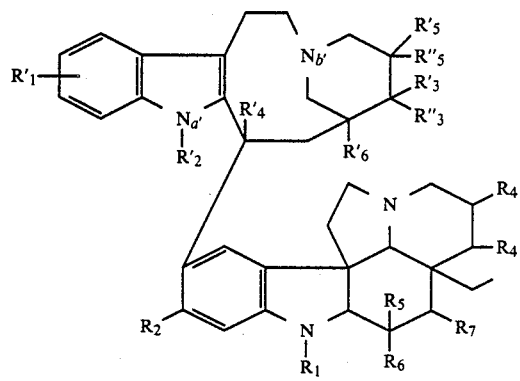

in which:

$R'_1$ represents a hydrogen atom or an alkoxy, acyl, formyl or haloacyl radical, $R'_2$ represents a hydrogen atom or a alkoyl radical, $R'_3$ and $R''_3$, identical or different, represent a hydrogen atom or a hydroxyl, alkanoyloxyl radical or, $R'_3$ and $R''_3$ together form a carbonyl grouping, or $R'_3$ and $R'_5$ together form an epoxy bridge or a double bond, $R'_4$ represents a hydrogen atom or an alkanoyloxy carbonyl, hydroxy methyl or alkanoyloxy methyl radical, $R'_5$ and $R''_5$ identical or different, represent a hydrogen atom or a hydroxyl, alkanoyloxyl, ethyl or hydroxy-2 ethyl radical, $R'_6$ represents a hydrogen atom or an ethyl, hydroxy-2 ethyl or acetyl radical, $R_1$ represents a hydrogen atom or an alkoyl formyl or acyl radical, $R_2$ represents a hydrogen atom or an alkoxy radical, $R_3$ represents a hydrogen atom or a hydroxyl or alkanoyloxyl radical or alternatively $R_3$ and $R_4$ together form an epoxy bridge or a double bond, $R_4$ represents a hydrogen atom or a hydroxyl or alkanoyloxyl radical or alternatively $R_4$ and $R_5$ together form an epoxy bridge, $R_6$ represents an alkanoyloxy carbonyl, hydrazidoacetamido, hydroxymethyl or alkanoyloxyl radical, $R_5$ and $R_7$ represent a hydrogen atom or a hydroxyl or alkanoyloxyl radical, Together with their salts of addition with the acids and their quaternary ammonium salts.

The alkoyl radicals mentioned in the present specification are preferably straight or branched lower alkoyl radicals having from 1 to 5 carbon atoms, such as methyl and ethyl radicals.

The alkoxy radicals mentioned in the present specification are preferably lower alkoxy radicals corresponding to the preceeding alkoyl radicals, i.e. ethoxy and methoxy radicals.

The acyl radicals mentioned in the present specification are for example acyl radicals arising from saturated or unsaturated lower carboxylic acids, such as acetyl and propionyl radicals.

In the same way the alkanoyloxy radicals are preferably radicals corresponding to the preceeding acyl radicals, such as acetyloxy radical.

The alkoyloxycarbonyl radicals are preferably radicals in which the alkoyl part corresponds to the above preferred definition, for example methoxycarbonyl radical.

Of the salts of addition and the quaternary ammonium salts, it is preferred that non-toxic pharmaceutically acceptable salts be prepared such as the salts of inorganic acids such as hydrochloric acid, or of organic acids such as acetic acid.

The present invention relates to a process for the preparation of a compound of formula I, characterised in that a compound of the formula II

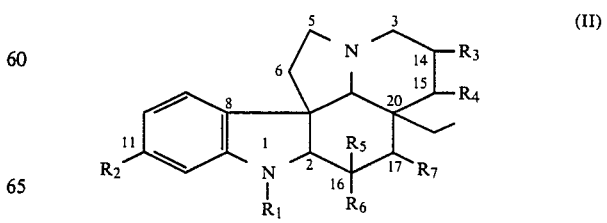

is made to react with a compound of formula III

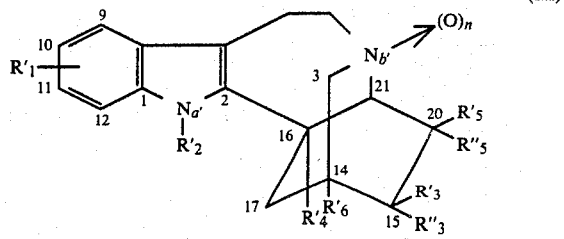

(III)

in these formulae, the various substituents have the meaning given for formula I and n is the whole number 0 or 1, in the presence iof an immonium ion forming reagent and in that the immonium ion obtained of the general formula IV:

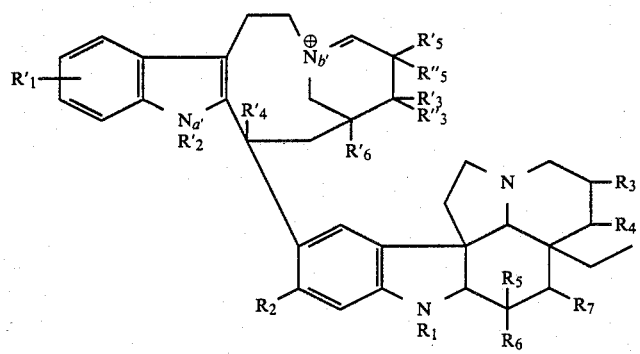

(IV)

in which the substituents have the meaning given above, is reduced to obtain the compound of formula I.

Preferred immonium ion forming agents are the halides, anhydrides or salts of organic or inorganic acids in particular halogenated or unhalogenated (in particular fluorinated) carboxylic acids. Of the usable salts, the salts of mercury (II) should be mentioned.

The immonium ion forming reagents are for example acetic acid anhydride or trifluoroacetic acid anhydride, or mercury acetate or trifluoro acetate, or mercury tetracetate ethylenediamine.

The immonium ion of formula IV is of course neutralised in the reaction mixture by the anion from the immonium ion forming reagent.

Generally the immonium ion of the general formula IV is obtained by treating the mixture of the alkaloide of general formula II and of the alkaloide of general formula III, or of the Nb'-oxide of the latter, in solution in an organic solvent with an excess of the immonium ion forming reagent. Preferably as the organic solvent a chlorinated solvent such as methylene chloride, dichloroethane or chloroform is used.

The reduction of the immonium ion IV into a compound of the general formula I is preferably carried out by means of an alkaline borohydride such as sodium borohydride or by catalytic hydrogenation in the presence of a suitable catalyst. The reduction is generally carried out in an organic solvent such as an alcohol and more particularly methanol or ethanol.

The reduction stage may be conducted in the reaction mixture originating from the first stage of the process or alternatively it is possible to evaporate the solvent of the first stage before carrying out the reduction in another solvent.

The process according to the present invention has the advantage over the previously known processes of permitting the preparation directly of the products of which the $C_{16}$ configuration is identical to that of natural products, the compounds having an unnatural $C_{16}$ configuration manifesting little or no anti-tumoral properties.

The process according to the invention can lead to a mixture of constituents of the general formula I having the natural or unnatural configuration (in 16) which can be isolated and purified by physical or chemical methods such as chromatography, gel-filtration or crystallisation.

According to the present invention it is particularly advantageous to use as the alkaloide of the general formula II alkaloides of the Aspidospermane type such as vindoline ($R_1=CH_3$, $R_2=OCH_3$, $R_3$ and $R_4$ forming a double bond, $R_5=OH$, $R_6=COOCH_3$ and $R_7=O-COCH_3$), desacetyl vindoline, dishydrovindolinc, vindorosine ($R_1=CH_3$, $R_2=H$, $R_3$ and $R_4$ form a double bond, $R_5=OH$, $R_6=COOCH_3$ and $R_7=OCOCH_3$), methoxy-11-dihydro-2,16-$N_a$-methyl tabersonine ($R_1=CH_3$, $R_2=OCH_3$, $R_3$ and $R_4$ form a double bond, $R_5=H$, $R_6=COOCH_3$ and $R_7=H$), or their derivatives and as alkaloides of the general formula (III), alkaloides of the Ibogane type such as coronaridine ($R'_1=R'_2=R'_3=R''_3=R'_5=R'_6=H$, $R'_4=COOCH_3$ and $R''_5=C_2H_5$), catharanthine ($R'_1=R'_2=R''_3=R'_6=H$, $R'_3$ and $R'_5$ together form a double bond, $R'_4=COOCH_3$ and $R''_5=C_2H_5$), allocatharanthine ($R'_1=R'_2=R''_3=R''_5=H$, $R'_3$ and $R'_5$ together form a double bond, $R'_6=C_2H_5$, $R'_4=COOCH_3$), dihydroallocatharanthine ($R'_1=R'_2=R''_3=R''_5=R'_3=R'_5=H$, $R'_6=C_2H_5$, $R'_4=COOCH_3$), voacangine ($R'_1=OCH_3$, $R'_2=R'_3=R'_5=R'_6=H$, $R'_4=COOCH_3$ and $R''_5=C_2H_5$), isovoacangine or conopharyngine or their derivatives preferably via their $N_b$-oxide.

When the starting compound of formula III is in its Nb'-oxide form the latter can be prepared by the oxidation of the compound of formula III in which n=0. As the oxidising agent one can use perbenzoic acids such as p-nitroperbenzoic acid.

The compounds of formula II or III are known or can be prepared by known processes.

Thus the following documents describe these compounds:

Vindoline—Catharanthus sp.

(1) K. Mothes, I. Richter, K. Stolle, D. Gröger, Naturwissenschaften, 52, 431 (1965).

Catharanthine—Catharanthus sp.

(2) N. R. Farnsworth, H. H. S. Fong, R. N. Blomster., Lloydia, 29, 343 (1966).

(3) M. Gorman, N. Neuss, J. J. Cone., J. Amer. Chem Soc., 87, 93 (1965).

Coronaridine—Catharanthus and Tabernaemontana sp. Ref. (3).

Allocatharanthine—dihydro-14,15-allocatharanthine (4) M. Muquet, N. Kunesch, J. Poisson., Tetrahedron., 28, 1363 (1972).

Vindorosine—Catharanthus (5) B. K. Moza, J. Trojanek, Coll. Czech. Chem. Comm., 28, 1419 (1963).

Dihydro-2,16-methoxy-11-tabersonine (6) C. Kan-Fan, B. C. Das, P. Potier, J. Lenuen, P. Boiteau., Ann. Pharm. pan., 26, 577 (1968).

Voacangine (7) M. B. Patel, J. Poisson, Bull. Soc. Chim. Fra., 427 (1966).

(8) A. A. Gorman, V. Agwada, M. Hesse, U. Renner, H. Schmid., Helv. Chim. Acta., 49, 2072 (1966).

Isovoacangine (9) M. P. Cava, S. K. Mowdood, J. L. Beal., Chem. and Ind., 2064 (1965).

Conopharyngine
Ref. (7).

The present invention also relates to the new semi-synthetic alkaloides of formula I, in particular those having the natural configuration, for example the compounds of formula I which may be obtained by the process according to the present invention and more particularly the following alkaloides which will be designated by the nature of the alkaloides which constitute them:

Vindoline or desacetyl vindoline or dihydro-14,15-dihydrovindoline-catharanthine.
Vindoline*-coronaridine.
Vindoline*-dihydro-15,20 catharanthine.
Vindoline*-dihydro-14,15 allocatharanthine.
Vindoline*-allocatharanthine.
Vindorosine-catharanthine.
$N_a$-methyl dihydro-2,16-methoxy-11-tabersonine-catharanthine.
Vindoline*-voacangine.
Vindoline*-isovoacangine.
Vindoline*-conopharyngine.
*- or desacetyl vindoline or dihydro-14,15-vindoline.

The present invention also relates to the alkaloides of formula I obtained by the process according to the present invention.

The following examples which are non-limitative show how the invention can be put into practice.

EXAMPLE 1

To 600 mg of catharanthine (III) ($R'_1=R'_2=R''_3=R'_6=H$, $R''_5=C_2H_5$, $R'_3-R'_5=\Delta$, $R'_4=COOCH_3$) in 18 cm$^3$ of anhydrous methylene chloride, are added at a temperature of 0° C. while stirring a 98% solution of 490 mg of p-nitroperbenzoic acid in 62 cm$^3$ of methylene chloride. After 5 min of contact, the reaction mixture was dissolved by 50 cm$^3$ of 10% aqueous solution of sodium carbonate and extracted by 3 times 200 cm$^3$ of methylene chloride. The organic phase was washed with 50 cm$^3$ of 10% aqueous solution of sodium carbonate and 50 cm$^3$ of water then dried on anhydrous sodium sulphate. After filtration the solvent was evaporated under reduced pressure (15 mm of mercury) at a temperature lower than 40° C. The Nb'-oxide of catharanthine was obtained with a quantitative yield.

To a solution of 210 mg of Nb'-oxide of catharanthine prepared as above and 285 mg of vindoline (II) ($R_1=CH_3$, $R_2=OCH_3$, $R_3-R_4=\Delta$, $R_5=OH$, $R_6=COOCH_3$, $R_7=OCOCH_3$) in 1.8 cm$^3$ of anhydrous methylene chloride maintained at 0° C., was added while stirring and operating in a nitrogen atmosphere, 0.25 cm$^3$ of trifluoroacetic anhydride. After 30 min of contact the solvent and excess trifluoroacetic anhydride were evaporated at reduced pressure (15 mm of mercury) at 20° C. The dry residue obtained was dissolved in 10 cm$^3$ of methanol and the solution obtained was cooled to 0° C. Then several times an excess of sodium borohydride was added. After 15 min at 0° C. the reaction mixture is dissolved by 100 cm$^3$ of water and the solution is extracted by 2 times 100 cm$^2$ and 2 times 50 cm$^3$ of chloroform. The organic phase was washed by 30 cm$^3$ of water and dried on anhydrous sodium sulphate. After filtration the solution was concentrated dry at reduced pressure (15 mm of mercury). The crude product obtained (492 mg) was separated into its constituents by chromatography on a thick layer of silica using the following elutriant systems:

chloroform-methanol (97-3 in volume)
ethyl acetate-ethanol (3-1 in volume)

In this way, in order of decreasing polarity, two compounds of the general formula (I) were separated (I-1 and I-2) in which the different symbols defined above are the same for the two compounds:

$\Delta^{15'}$-deshydroxy-20'vincaleucoblastine I-1

195 mg, crystallised in methanol, M.P. (dec.)=208°-210° C. $[\alpha]_D^{22} = +19°$ (c=0.70, CHCl$_3$).

IR: ($\nu$ cm$^{-1}$) (CHCl$_3$/film): 1740 (esters), 1615 (indoline).

UV: (EtOH $\lambda$ nm): 263 (17,500), 290 (14,300), 297 (13,400) (super-imposition of chromophores indole and dihydroindole).

Mass spectrum: peaks at m/e: 792 (M$^{+\cdot}$), 761, 733, 670, 633, 611, 525, 469, 336, 282, 135, 121.

RMN spectrum: 240 Mz (CDCl$_3$; $\delta$ ppm; TMS=0) J (hertz): 9.77 (1H, C$_{16}$—OH); 7.87 (s 1H) N$_a$—H; 6.52 (s 1H) and 6.03 (s 1H): C$_9$—H and C$_{12}$—H; 5.76 (m 1H) and 5.22 (d, 1H, J=9.4) C$_{14}$—H and C$_{15}$—H; 5.37 (s) C$_{17}$—H; 3.74 (s 3H), 3.70 (s 3H) and 3.55 (s 3H): C$_{16}$—CO$_2$CH$_3$, C$_{16'}$—CO$_2$CH$_3$ in C$_{11}$—O—CH$_3$; 2.65 (s 3H) N$_a$—CH$_3$; 2.07 (s 3H) OCOCH$_3$; 0.96 (t 3H) and 0.81 (t 3H): C$_{18'}$—H and C$_{18}$—H.

Spectrum of circular dichroism (C.D.) $\lambda$ nm ($\Delta\epsilon$): 305(+6.5), 258(+14.0);

I-2=epi-16' I-1

48 mg. M.P. (hydrobromide): >260° C. $[\alpha]_D^{22°} = -86.4°$ (c=0.72; CHCl$_3$).

IR: 1740 (esters), 1620 (indoline).

UV: (EtOH): 263 (12,600), 289 (10,700), 297 (11,500): super-imposition of chromophores indole and dihydroindole.

Mass spectrum: peaks at m/e: 792 (M$^{+\cdot}$), 733, 670, 633, 610, 525, 469, 336, 282, 135, 121.

RMN spectrum: 8.99 (s 1H, Na'—H), 6.85 (s 1H) and 5.92 (s 1H): C$_9$—H and C$_{12}$—H; 5.84 (m 1H), 5.50 (m 1H) and 5.24 (d, 1H, J=9.4) C$_{14}$—H, C$_{15'}$—H and C$_{15}$—H; 5.28 (s 1H): C$_{17}$—H; 3.86 (s 3H) and 3.74 (s enlarged, 6H): C$_{16}$—CO$_2$CH$_3$, C$_{16'}$—CO$_2$CH$_3$ and C$_{11}$—OCH$_3$; 2.60 (s 3H) N$_a$—CH$_3$; 2.07 (s 3H) O—COCH$_3$; 1.00 (t 3H) C$_{18'}$—H and 0.60 (t 3H) C$_{18}$—H.

Circular dichlroism spectrum (C.D.) λ nm (Δε): 309(+8.5), 258(−13);

EXAMPLE 2

To a solution of 0.50 m mol of $N_b$-oxide of coronaridine prepared as for Example 1 and 0.51 m mol of vindoline in 15 cm³ of anhydrous methylene chloride were added at 0° while stirring, 2 cm³ of trifluoroacetic anhydride and the mixture was left to return to the ambient temperature. After 1 hour of contact the solvents were distilled at reduced pressure and ambient temperature. The product obtained dissolved in 10 cm³ of methanol was reduced at 0° with sodium borohydride (15 min). After the usual treatment, the constituents of the crude product obtained were separated by chromatography on a thick layer of silica, using several elutriant systems.

I-3-($R_1=CH_3$, $R_2=OCH_3$, $R_3+R_4=$double bond, $R_5=OH$, $R_6=COOCH_3$, $R_7=OCOCH_3$, $R_1'=R_2'=R_5'=H$, $R''_5=C_2H_5$—20S, $R_4'=COOCH_3$).

173 mg, crystallised in acetone: M.P. decomposition 275°,

I.R. ($\nu$ cm$^{-1}$, CHCl₃): 1740 (esters), 1620 (indoline)

U.V. [EtOH, $\lambda_{max}$ nm ($\epsilon$)]: 264 (12600), 291 (11900), 297 (11900 super-imposition of chromophors indole and dihydroindole.

R.M.N. spectrum: 9.60 (1H, $C_{16}$—OH); 8.75 (s, 1H, $N_{a'}$—H); 7.3-6.85 (aromatic protons) 6.90 (s) and 5.97 (s, 1H) $C_9$—H and $C_{12}$—H; 5.71 (dd, 1H, J~9.5 and 3, $C_{14}$—H); 5.20 (s, 1H, $C_{17}$—H); 5.00 (d, 1H, J~9.5, $C_{15}$—H); 3.87 (s 3H) 3.72 and 3.70 (2s, 6H) $C_{11}$—OCH₃, $C_{16}$—CO₂CH₃ and $C_{16'}$—CO₂CH₃; 2.63 (s, 3H, $N_a$—CH₃); 1.99 (s, 3H, OCOCH₃); 0.92 (t, 3H, J~7) and −0.12 (t. 3H, J~7) $C_{18'}$—H and $C_{18}$—H.)

C.D.: 312 (−11.5); 296 (−4.6); 284 (−4.6); 263 (+31.2)

I-4-epi 16' and/or epi 20' I-3: 44 mg, crystallised in an acetone-ether mixture: M.P. decomposition 218°-220° $[\alpha]_D=-66°$ (c=0.93, CHCl₃).

I.R.: 1740 and 1620.

U.V. (EtOH): 264 (13400), 291 (11200), 298 (11400).

R.M.N. Spectrum: 9.64 (1H, $C_{16}$—CH); 8.78 (s, 1H, $N_{a'}$—H): 7.5-6.8 (aromatic protons); 6.85 (s, 1H) and 6.02 (s, 1H) $C_9$—H and $C_{12}$—H; 5.72 (dd, 1H, J=10 and 4, $C_{14}$—H); 5.23 (s, 1H, $C_{17}$—H); 5.02 (d, 1H, J=10, $C_{15}$—H); 3.89 (s, 3H) and 3.74 (s enlarged, 6H) $C_{11}$—OCH₃, $C_{16}$—CO₂CH₃ and $C_{16'}$—CO₂CH₃; 2.64 (s, 3H, $N_a$—CH₃); 2.00 (s, 3H, OCOCH₃); 0.92 (t, 3H, J~7) and −0.12 (t, 3H, J~7) $C_{18'}$—H and $C_{18}$—H.

C.D.: 310 (−9.92); 294 (=2.88); 280 (−2.94); 257 (+34).

I-5-epi-16' and/or epi-20' I-3.

17 mg, amorphous; $[\alpha]_D=-158°$ (c=0.5, CHCl₃).

IR: 1740, 1615.

U.V. (EtOH): 258 (11,600), 291 (10,700), 298 (10,700).

Mass spectra of I-3, I-4, I-5: peaks at m/e 794 (M$^+$·), 763, 735, 635, 610, 469, 338, 282, 222, 188, 138 (base peak), 135, 124, 122, 121, 107.

C.D.: 306 (−7.32); 288 (−2.50); 260 (+3.9).

EXAMPLE 3

To a solution of 120 mg (3.38×10$^{-4}$) mol of dihydrocatharanthine N-oxide prepared in the conditions described in Example 1 for the preparation of the Nb oxide of catharanthine and 162 mg (3.55×10$^{-4}$) mol of vindoline in 0.99 cm³ of anhydrous methylene chloride are added at −78° under agitation and in argon, 0.134 ml of trifluroacetic anhydride. The substances are left in contact for 50 min at this temperature. The solvents are evaporated at reduced pressure and ambient temperature. The product, dissolved in 6 ml of methanol is reduced at 0° by sodium borohydride. After the usual treatment, the crude product obtained is purified by chromatography on a thick layer of silica (elutriant ethyl 1,3 ethanol acetate, then ethyl 92-8 methanol acetate).

I-6 ($R_1=CH_3$, $R_2=OCH_3$, $R_3+R_4=$double bond, $R_5=OH$, $R_6=COOCH_3$, $R_7=OCOCH_3$, $R_1'=R_2'=R_5'=R_3'=R''_3=R_6'=H$, $R''_5=C_2H_5$ (20'S), $R_4'=COOCH_3$ (16'S).

26 mg. M.P.=214° (methanol) $[\alpha]_D=+69°$. (c=0.43, CHCl₃).

I.R.: 1740, 1615.

U.V.: 263 (11,900, 290 (10,770), 297 (10,208).

RMN (240 MHz): 9.77 (1H) $C_{16}$—OH; 7.83 (Na'H); 7.03 (aromatic protons) 6.49 (s 1H) and 6.02 (s 1H) $C_9$—H and $C_{12}$—H; 5.78 $C_{14}$—H; 5.36 (s, 1H) $C_{17}$—H; 5.23 (d 1H, J=9) $C_{15}$—H; 3.74 (s 6H) and 3.55 (s 3H) $C_{16}$—COOCH₃, $C_{16'}$—COOCH₃ and $C_{11}$—OCH₃; 2.67 (s 3H) $N_a$—CH₃, 2.08 (s 3H) $C_{17}$—OCOCH₃ 0.86 and 0.82 (2t superimposed $C_{18'}$—H and $C_{18}$—H.

C.D.: 302 (+5); 255 (+12.5).

I-7=[I-6 (16'R, 20'S)] or epi-16' I-6

55 mg. Amorphous $[\alpha]_D=-26°$. (c=0.58, CHCl₃).

IR: 1740, 1618.

UV: 264 (11,600), 290 (9,900), 297 (10,300).

RMN (240 MHz): 9.62 (1H, $C_{16}$—OH); 8.95 ($N_{a'}$—H); 7.39-7.04 aromatic protons; 6.93 (s 1H) and 6.00 (s 1H) $C_9$—H and $C_{12}$—H; 5.37 (s 1H) $C_{17}$—H; 5.90 and 5.38 (2 m, 1H) $C_{14}$—H and $C_{15}$—H; 3.98 (s 3H) and 3.68 (s, 6H) $C_{16}$—COOCH₃, $C_{16'}$—COOCH₃ and $C_{11}$—OCH₃; 2.58 (s 3H) $N_a$—CH₃; 2.05 (s 3H) $C_{17}$—OCOCH₃) 0.91 (t 3H) and 0.67 (t 3H) $C_{18}$—H and $C_{18'}$—H.

C.D.: 307 (+8.2); 282 (+5); 260 (−13.8).

I-8=[I-6 (16'R, 20'R)], or epi-20' I-7 12 mg Amorphous $[\alpha]_D=-53°$. (c=0.60, CHCl₃).

IR: 1740, 1620

UV: 264 (12,730), 290 (11,250), 298 (11,460).

RMN (240 MHz): 8.83 ($N_{a'}$—H); 7.2 to 6.9 aromatic protons; 6.56 (s 1H) and 5.91 (s 1H) $C_9$—H and $C_{12}$—H; 5.85 and 5.24 (2m 2H) $C_{14}$—H and $C_{15}$—H; 5.19 (s 1H) $C_{17}$—H; 3.83 (s 3H); 3.68 (s 1H), 3.66 (s 3H); $C_{16}$—COOCH₃; $C_{16'}$—COOCH₃ and $C_{11}$—OCH₃; 2.60 (s 3H) $N_a$—CH₃; 2.04 (s 3H) $C_{17}$—OCOCH₃; 0.9 (t 3H) and 0.63 (t 3H) $C_{18}$—H and $C_{18'}$—H.

C.D.: 310 (+5.85); 280 (+3.2); 259 (−11.8).

Mass spectrum: I-6, I-7, I-8: M$^+$ at m/e 794, 763, 735, 635, 469, 338, 282, 138, 136, 124, 122, 121.

EXAMPLE 4

To a solution of 100 mg (2.82×10$^{-4}$ mol) of Nb oxide of dihydroallocatharanthine and of 135 mg (2.94×10$^{-4}$ mol) of vindoline in 0.82 cm³ of anhydrous methylene chloride is added at −78° under agitation and in argon 0.1 ml of trifluoroacetic anhydride. After the usual treatment, 26 mg of I-9 are isolated by chromatography on a thick layer of silica (alkaline silica, ethyl 97-3 methanol acetate). I-9 ($R_1=CH_3$; $R_2=OCH_3$; $R_3$ and $R_4=$double bond, $R_5=OH$; $R_6=COOCH_3$; $R_7=OCOCH_3$. $R_1'=R_2'=R_3'=R''_5=R''_3=H$, $R_4'=COOCH_3$ (16.5); $R_6'=C_2H_5$).

$[\alpha]_D=+13°$ (c=0.53; CHCl₃)

IR: 1745, 1620

UV: 259 (15,300), 288 (12,300), 297 (11,200).

RMN: 9.73 (s 1H) $C_{16}$—OH; 7.92 (s 1H) $N_a$—H; 6.84 (s 1H) $C_9$—H; 6.04 (s 1H) $C_{12}$—H; 5.88 and 5.34 (2d, 1H) $C_{14}$—H and $C_{15}$—H; 5.47 (s 1H) $C_{17}$—H; 3.97 (2s 6H) and 3.66 (s 3H) $C_{16}$—COOCH$_3$, $C_{16'}$—COOCH$_3$ and $C_{11}$—OCH$_3$; 2.79 (s 3H) $N_a$—CH$_3$; 2.25 (s 3H) OCOCH$_3$; 0.92 (t 3H) $C_{18}$—H and 0.47 (3H) attributed to $C_{18'}$—H.

C.D.: 305 (+7.3); 259 (+14.6).

Mass spectrum: M+ at m/e 794, 762, 735, 663, 634, 468, 338, 282, 135, 124.

EXAMPLE 5

To a solution of 85 mg ($2.41 \times 10^{-4}$ mol) of Nb oxide of allocatharanthine and of 114 mg ($2.5 \times 10^{-4}$ mol) of vindoline in 0.70 cm$^3$ of anhydrous methylene chloride at 0° C. under agitation and in argon, are added 0.09 cm$^3$ of trifluroacetic anhydride—contact time 30 min—then the substances are reduced with sodium borohydride in methanol and the usual treatment is carried out.

Using chromatography on a thick layer of silica (neutral silica chloroform-methanol 95-5) 37 mg of I-10 are isolated.

I-10 ($R_1$=CH$_3$; $R_2$=OCH$_3$; $R_3$ and $R_4$=double bond; $R_5$=OH; $R_6$=COOCH$_3$; $R_7$=O-COCH$_3$=$R'_1$=$R'_2$=$R''_3$=$R''_5$=H; $R'_3$ and $R'_5$=double bond; $R'_4$=COOCH$_3$ (16.5); $R'_6$=C$_2$H$_5$).

$[\alpha]_D \sim 0°$ (c=0.85; CHCl$_3$)
IR: 1740, 1620
UV: 263 (13,300), 291 (8,600), 298 (9,000).

RMN (60 MHz): 7.8–7.4 (2H) $C_{16}$—OH and $N_a$—H; 7.4–6.90 (aromatic protons); 6.0 (s 1H) $C_9$—H or $C_{12}$—H; 5.4 (s 1H) $C_{17}$—H; 3.8 (s 3H), 3.6 (s 3H), 3.5 (s 3H) $C_{16}$—COOCH$_3$, $C_{16'}$—COOCH$_3$ and $C_{11}$—OCH$_3$; 2.7 (s 3H) $N_a$—CH$_3$; 2.1 (s 3H) $C_{17}$—OCOCH$_3$; 0.8–0.4 (2t, 6H) $C_{18}$—H and $C_{18'}$—H.

C.D.: 302 (+7.9), 258 (+0.18).

Mass spectrum: M+ at m/e: 792, 763, 733, 631, 539, 469, 394, 379, 282, 135, 122, 121.

EXAMPLE 6

To a solution of 50 mg ($1.42 \times 10^{-4}$ mol) of Nb oxide of catharanthine and 63 mg ($1.49 \times 10^{-4}$ mol) of vindorosine in 0.4 cm$^3$ of anhydrous methylene chloride are added at 0° in argon, 0.05 cm$^3$ of trifluoroacetic anhydride—contact time 50 min, then usual treatment.

Using chromatography on a thick layer of silica (neutral silica chloroform-methanol 98-2) 20 mg of I-11 are isolated.

$[\alpha]_D = -40°$ (c=0.5, CHCl$_3$).

I-11 ($R_1$=CH$_3$; $R_2$=H; $R_3$ and $R_4$=double bond; $R_5$=OH; $R_6$=COOCH$_3$; $R_7$=OCOCH$_3$. $R'_1$=$R'_2$=$R'_6$=$R''_3$=H; $R'_5$ and $R'_3$=double bond $R''_5$=C$_2$H$_5$ $R'_4$=COOCH$_3$).

IR: 1745, 1620
UV: 262 (14,300), 286 (11,200), 294 (10,400).

RMN (240 MHz): 9.12 ($C_{16}$—OH); 6.83 (s enlarged $C_9$—H); 6.34 (d 1H, J=8.5) $C_{12}$—H; 5.77 (m 2H) $C_{14}$—H and $C_{15'}$—H; 5.34 (s 1H) $C_{17}$—H; 5.15 (d 1H, $J_{14,15}$=10) $C_{15}$—H; 3.82 and 3.79 (2s, 6H) $C_{16}$—COOCH$_3$, $C_{16'}$—COOCH$_3$; 2.70 (s 3H) $N_a$—CH$_3$; 2.11 (s 3H) $C_{17}$—OCOCH$_3$; 1.07 (t 3H, J~7), $C_{18'}$—H; 0.27 (t 3H, J~6.5) $C_{18}$—H.

EXAMPLE 7

To a solution of 100 mg ($2.48 \times 10^{-4}$ mol) of Nb-oxide of catharanthine and 114 mg ($2.98 \times 10^{-4}$ mol) of $N_a$-Me dihydro-2,16 methoxy-11-tabersonine in 0.82 ml of anhydrous methylene chloride at −78° in argon are added 0.110 ml of trifluoroacetic anhydride—contact time 1 hour—usual treatment.

Purification by chromatography on thick layer of silica (neutral silica chloroform-methanol 97-3). 40 mg of I-12.

$[\alpha]_D = +87°$ (c=0.42; CHCl$_3$)

I-12 ($R_1$=CH$_3$; $R_2$=OCH$_3$; $R_3$ and $R_4$=double bond; $R_5$=H; $R_6$=COOCH$_3$; $R_7$=H; $R'_1$=$R'_2$=$R''_3$=$R'_6$=H, $R'_3$ and $R'_5$=double bond; $R''_5$=C$_2$H$_5$, $R'_4$=COOCH$_3$ (16.5).

IR: 1740, 1625
UV: 268 (14,000), 290 (11,600), 294 (11,200).

RMN (240 MHz): 7.95 (s 1H) $N_{a'}$—H; 6.55 (s 1H) and 6.08 (s 1H) $C_9$—H and $C_{12}$—H; 5.70 (dd 1H); 5.45 (m 1H) and 5.32 (dd 1H) $C_{14}$—H, $C_{15'}$—H and $C_{15}$—H; 3.85, 3.78 and 3.65 (3s 3H) $C_{16'}$—COOCH$_3$, $C_{16}$—COOCH$_3$ and $C_{11}$—OCH$_3$; 2.80 (s 3H) $N_a$—CH$_3$, 1.22 and 0.99 (2t 3H) $C_{18}$—H and $C_{18'}$—H.

C.D.: 305 (+5.8); 263 (+13.4).

Mass spectrum: M+ at m/e 718, 687, 659, 536, 395, 336 (100%), 295, 293, 135, 122.

The present invention also relates to medicinal compounds containing at least one new bis-indolic compound or one of its salts, in association with any other pharmaceutically compatitible produce, which may be inert or physiologically active.

These compositions may be present in any form which is appropriate to the method of administration foreseen.

The parenteral method is the preferred method of administration, in particular the intravenous method.

The composition according to the invention for parenteral administration may be aqueous or non-aqueous sterile solutions, suspension or emulsions. As a solvent or vehicle it is possible to use propylene glycol, polyethylene glycol, vegetable oils, in particular olive oil, injectable organic esters, in particular ethyl oleate. These compositions may also contain adjuvants in particular wetting, emulsifying and dispersing agents. Sterilisation can be carried out in several ways, for example using a bacteralogical filter, by incorporating sterilising agents into the composition, by irradiation or heating. They may also be prepared in the form of sterile solid compositions which can be dissolved or dispersed at the time of use in sterile water or any other injectable sterile medium.

The new bis-indolic compounds or their salts are active in the treatment of cancer, namely solid tumors or leukemia in daily doses of between 10 and 20 mg per day for an adult.

The following example illustrates a composition according to the invention:

EXAMPLE

A solution is prepared containing 10 mg/cm$^3$ of active material by dissolving 1 g of the product I-1 of Example 1 in 100 cm$^3$ of apyrogenic physiological solution. The solution obtained is distributed aseptically into 2 cm$^3$ ampoules with 1 cm$^3$ per ampoule. The ampoules are sealed and each contain 10 mg of active principle.

We claim:

1. A process for the preparation of compounds of the formula:

in which:

R'₁ = H or OCH₃;
R'₂ is H or an alkyl group of 1 to 5 carbon atoms,
R'₃ is H, R"₃ is H, R'₅ is H, or alternatively R'₃ and R'₅ together form a double bond;
R'₄ is H or methoxycarbonyl;
R"₅ is H or ethyl;
R'₆ is H or ethyl;
R₁ is H or an alkyl group of from 1 to 4 carbon atoms;
R₂ is H or methoxy;
R₃ and R₄ are each H or alternatively together form a double bond;
R₅ is H, OH or OAc;
R₆ is H, methoxycarbonyl, hydrazino, or acetamide; and
R₇ is H, acetyloxy or OH; together with their salts of addition and quaternary ammonium salts;
(a) coupling a compound of the formula:

with a compound of the formula:

in which R₁, R₂, R₃, R₄, R₅, R₆, R₇, R'₃, R"₃, R'₄, R'₅, R"₅, R'₆ are defined as above, in the presence of an immonium ion forming reagent selected from the group consisting of halide, anhydride or salt of carboxylic acids to form an immonium ion; and
(b) reducing said immonium ion.

2. The process of claim 1 wherein said immonium ion forming reagent is selected from the group consisting of halide, anhydride or salt of acetic acid.

3. The process of claim 2 wherein step (a) is performed by reacting compound II with compound III with an excess of immonium ion forming reagent in an organic solvent.

4. A process according to claim 3, characterised in that the organic solvent is chosen from the group of methylene chloride, dichloroethane or chloroform.

5. The process of claim 1 wherein step (b) is effected by an alkaline borohydride in an alcohol.

6. A process according to claim 1, characterised in that the products obtained have at the level of the carbon 16' the configuration of the natural alkaloids of the vinblastine type.

7. A process according to claim 1, characterised in that as the alkaloide of the general formula II the following may be used: vindoline, desacetyl vindoline, dihydro-14,15-vindoline, vindorosine or dihydro-2,16-Na-methyl methoxy-11 tabersonine and as the alkaloide of the general formula III the following may be used: coronaridine, catharanthine, allocatharanthine, dihydrocatharanthine, dihydroallocatharanthine, voacangine, isovoacangine or conopharyngine.

8. The process of claim 1 wherein the compound of formula II is vindoline and the compound of formula III is N-oxide of catharanthine.

9. The process of claim 8 wherein the immonium ion forming reagent is trifluoracetic anhydride.

10. A process for the synthesis of a dimer derived from an indole unit of the natrual Iboga alkaloid family containing an aza-bicyclo-octane portion and a dihydroindole unit of the natural Aspidosperma and Vinca alkaloid family, the sterochemistry of the carbon-carbon linkage between these units being identical with that of vinblastine which consists of:
(a) forming an N-oxide intermediate from said indole unit by oxidizing the bridge nitrogen;
(b) treating said N-oxide indole intermediate in the presence of one member of the group consisting of acetic anhydride, halogenated acetic anhydride and acetyl chloride to effect a Polonovski-type fragmentation reaction;
(c) without isolating the product of step (b), coupling said reaction produce with a dihydroindole unit in the presence of acetic anhydride, halogenated acetic anhydride or acetyl chloride at a low temperature of about −10° C. to +10° C. under inert conditions; and
(d) subsequently reducing the immonium nitrogen on the indole unit by reacting with alkali metal borohydride to produce the dimer.

* * * * *